US009439769B2

(12) United States Patent
Wirth et al.

(10) Patent No.: US 9,439,769 B2
(45) Date of Patent: Sep. 13, 2016

(54) MOBILE BEARING GLENOID PROSTHESIS (71) Applicant: DePuy Synthes Products, LLC, Raynham, MA (US)

(72) Inventors: Michael A. Wirth, San Antonio, TX (US); Joseph P. Iannotti, Strongsville, OH (US); Gerald R. Williams, Jr., Villanova, PA (US); Kyle E. Lappin, Fort Wayne, IN (US); Matthew T. Stone, Warsaw, IN (US)

(73) Assignee: DePuy Synthes Products, Inc., Raynham, MA (US)

( * ) Notice: Subject to any disclaimer, the term of this patent is extended or adjusted under 35 U.S.C. 154(b) by 76 days.

(21) Appl. No.: 14/507,446

(22) Filed: Oct. 6, 2014

(65) Prior Publication Data
US 2015/0025642 A1 Jan. 22, 2015

Related U.S. Application Data (63) Continuation of application No. 13/094,180, filed on Apr. 26, 2011, now Pat. No. 8,882,845.

(60) Provisional application No. 61/331,458, filed on May 5, 2010.

(51) Int. Cl.
*A61F 2/40* (2006.01)
*A61F 2/30* (2006.01)

(52) U.S. Cl.
CPC ........ *A61F 2/4081* (2013.01); *A61F 2002/305* (2013.01); *A61F 2002/30125* (2013.01);
(Continued)

(58) Field of Classification Search
CPC .......... A61F 2/32; A61F 2/34; A61F 2/4081; A61F 2002/30125; A61F 2002/305; A61F 2002/30364
See application file for complete search history.

(56) References Cited

U.S. PATENT DOCUMENTS

| 4,261,062 A | 4/1981 | Amstutz et al. |
| 6,911,047 B2 | 6/2005 | Rockwood |

(Continued)

FOREIGN PATENT DOCUMENTS

| EP | 1598034 A1 | 11/2005 |
| EP | 1639967 A1 | 3/2006 |

(Continued)

OTHER PUBLICATIONS

English Translation of Notification of Reasons for Refusal corresponding to Japanese Patent Application No. 2013-509211, mailed Dec. 2, 2014 (3 pages).

(Continued)

*Primary Examiner* — Brian Dukert
(74) *Attorney, Agent, or Firm* — Maginot, Moore & Beck, LLP (57) ABSTRACT

A method of installing a prosthesis assembly includes installing a base component in a prepared glenoid vault, axially aligning a plurality of slots in one of a stretched glenoid bearing component and a base component with a plurality of ridges in the other of the glenoid bearing component and the base component, each of the plurality of slots having a maximum length which is greater than a maximum length of a respective one of the plurality of ridges, engaging each of the plurality of ridges with the respective one of the plurality of grooves thereby rotatably coupling the glenoid bearing component and the base component and limiting axial movement of the glenoid bearing component relative to the base component, and placing the bearing surface into articulating contact with a humeral head.

17 Claims, 11 Drawing Sheets

(52) U.S. Cl.
CPC ............... *A61F2002/30332* (2013.01); *A61F 2002/30364* (2013.01); *A61F 2002/30934* (2013.01); *A61F 2220/0025* (2013.01); *A61F 2220/0033* (2013.01); *A61F 2230/0008* (2013.01)

(56) References Cited

U.S. PATENT DOCUMENTS

| | | | |
|---|---|---|---|
| 8,231,683 B2 * | 7/2012 | Lappin | A61F 2/4081 623/19.11 |
| 2001/0037153 A1 | 11/2001 | Rockwood et al. | |
| 2005/0049709 A1 | 3/2005 | Tornier | |
| 2006/0069443 A1 | 3/2006 | Deffenbaugh et al. | |
| 2007/0100463 A1 | 5/2007 | Aram et al. | |
| 2007/0106390 A1 | 5/2007 | Richards | |
| 2010/0331990 A1 | 12/2010 | Mroczkowski et al. | |

FOREIGN PATENT DOCUMENTS

| | | |
|---|---|---|
| EP | 1787603 A1 | 5/2007 |
| FR | 2755847 A1 | 5/1998 |
| FR | 2825263 A1 | 12/2002 |
| GB | 2297257 A | 7/1996 |
| JP | H11-042244 A | 2/1999 |
| JP | 2007-503861 A | 3/2007 |

OTHER PUBLICATIONS

International Search Report in corresponding PCT Application (i.e., PCTUS2011/035144) mailed Aug. 1, 2011 (5 pages).

* cited by examiner

MOBILE BEARING GLENOID PROSTHESIS

This application is a utility application claiming priority to U.S. patent application Ser. No. 13/094,180, filed Apr. 26, 2011, entitled "Mobile Bearing Glenoid Prosthesis" (now U.S. Pat. No. 8,882,845, issued Nov. 11, 2014), which in turn claims priority to U.S. Provisional Application No. 61/331,458, filed May 5, 2010, entitled "Mobile Bearing Glenoid Prosthesis," the disclosures of which are both incorporated by reference herein in their entirety.

BACKGROUND

The present disclosure relates generally to shoulder prostheses, and more particularly to shoulder prostheses configured for use in shoulders having glenoid vault erosion or defects.

Figure 1:
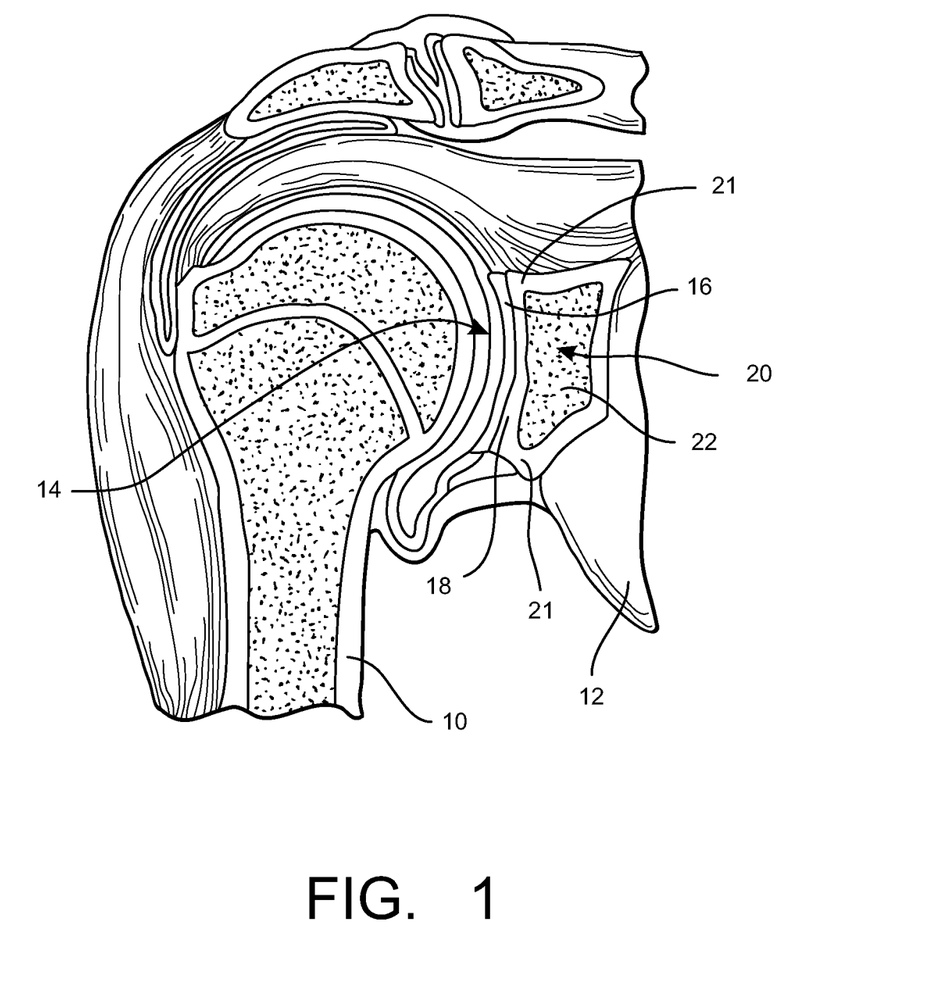
FIG. 1 depicts a cross-sectional view of an anatomically normal glenohumeral joint of a human patient.

A typical shoulder or glenohumeral joint is formed in a human body where the humerus 10 movably contacts the scapula 12 as shown in FIG. 1. The scapula 12 includes a glenoid fossa 14 that forms a socket against which the head of the humerus 10 articulates. At this socket, the scapula 12 includes cartilage 16 that facilitates such articulation. Beneath the cartilage is subchondral bone 18 that forms a wall of a glenoid vault 20 that defines a cavity which contains cancellous bone 22. The subchondral bone 18 that forms the glenoid vault 20 defines a glenoid rim 21 at a periphery of the glenoid vault that is attached to the cartilage 16 (see FIG. 1). During the lifetime of a patient, the glenoid fossa 14 may become worn, especially at its posterior and/or superior portions thereby causing severe shoulder pain and limiting the range of motion of the patient's shoulder joint. To alleviate such pain and increase the patient's range of motion, a shoulder arthroplasty may be performed.

Shoulder arthroplasty often involves surgical replacement of the glenoid fossa with a conventional glenoid prosthesis such as the one disclosed in U.S. Pat. No. 6,911,047, the disclosure of which is herein incorporated by reference. The glenoid prosthesis, when implanted, provides a new laterally-facing bearing surface, which may be concave or convex, for articulation with a complementary bearing surface of a natural or prosthetic humeral head. Such conventional glenoid prosthesis is typically formed from UHMW polyethylene, titanium, or cobalt chrome and includes bone anchor(s) such as peg(s), screw(s), post(s), or a keel extending from a back side of the device opposite its bearing surface. So configured, the back side of the prosthesis is typically secured against subchondral bone of the glenoid vault while the bone anchor(s) may extend into the cavity of the glenoid vault whereby it may become anchored to cancellous bone located within the glenoid vault.

Shoulder prostheses such as those described above are very effective. During typical movement of the shoulder joint after arthroplasty, however, the humeral head rotates and slides against the glenoid surface. Glenoid components, however, are typically spherical in shape. Accordingly, the translation of the humeral head in the shoulder joint after arthroplasty can result in edge loading of the prosthesis assembly. Edge loading can result in limited motion, instability, and accelerated wear.

Some attempts have been made to reduce the problems associated with edge loading. Some prosthesis assemblies introduce a mismatch in the diameter of the head and the diameter of the glenoid component. This approach accommodates translation of the humeral head but does not eliminate edge loading. Additionally, the resulting loss of optimal coverage of the humeral head results in increased instability.

Another approach that has been used is to use varying diameters in the glenoid component. This approach also fails to eliminate edge loading and further results in reduced stability.

What is needed therefore is an improved prosthesis assembly for use in patients requiring shoulder arthroplasty. An improved prosthesis assembly which reduces edge loading without increasing instability of the shoulder joint is also needed.

SUMMARY

In accordance with one embodiment of the present disclosure, there is provided a prosthesis assembly configured for use with a scapula which includes a spherical humeral component, an elongated glenoid bearing including a first bearing surface with (i) a first spherical end portion with a first radius of curvature, (ii) a second spherical end portion with a second radius of curvature, and (iii) a central portion located between the first spherical end portion and the second spherical end portion, and a first coupling portion extending from a second bearing surface opposite the bearing surface, and a base configured to rotatably support the elongated glenoid bearing, wherein the first radius of curvature is substantially equal to the second radius of curvature and the central portion does not have a radius of curvature that is substantially equal to the second radius of curvature.

Pursuant to another embodiment of the present disclosure, a prosthesis assembly configured for use with a scapula includes a spherical humeral component, a stretched glenoid bearing including a first bearing surface with (i) a first spherical outer portion with a first radius of curvature, (ii) a second spherical outer portion with a second radius of curvature, and (iii) a central portion located between the first spherical outer portion and the second spherical outer portion, and a first mating portion extending from a second bearing surface opposite the first bearing surface, and a base including a third bearing surface and a second mating portion extending from the third bearing surface, the base configured to rotatably support the stretched glenoid bearing, wherein the first radius of curvature is substantially equal to the second radius of curvature and the central portion does not have a radius of curvature that is substantially equal to the second radius of curvature.

In one embodiment, a method of installing a prosthesis assembly includes installing a base component in a prepared glenoid vault, selecting a glenoid bearing component including a bearing surface comprising a first articulating portion partially surrounded by a first rim portion, a second articulating portion partially surrounded by a second rim portion, and a third articulating portion partially surrounded by a pair of spaced apart third rim portions, wherein the first rim portion, the second rim portion, and the pair of spaced apart third rim portions define a non-circular shape when projected onto a plane, and the first rim portion has a first radii of curvature on the plane, the second rim portion has a second radii of curvature on the plane, axially aligning a plurality of slots in one of the glenoid bearing component and the base component with a plurality of ridges in the other of the glenoid bearing component and the base component, each of the plurality of slots having a maximum length which is greater than a maximum length of a respective one of the plurality of ridges, engaging each of the plurality of ridges with the respective one of the plurality of grooves thereby rotatably coupling the glenoid bearing component and the base component and limiting axial movement of the glenoid bearing component relative to the base component, and placing the bearing surface into articulating contact with a humeral head.

In another embodiment, a method of installing a prosthesis assembly includes installing a base component in a prepared glenoid vault, selecting a glenoid bearing component including a first bearing surface comprising a first articulating portion partially surrounded by a first rim portion, a second articulating portion partially surrounded by a second rim portion, and a third articulating portion partially surrounded by a pair of spaced apart third rim portions, wherein the first rim portion, the second rim portion, and the pair of spaced apart third rim portions define a non-circular shape when projected onto a plane, axially aligning a first locking component of the glenoid bearing component and a second locking component of the base component along an axis perpendicular to the plane, engaging the first locking component with the second locking component by moving the glenoid bearing component along the axis thereby rotatably coupling the glenoid bearing component and the base component and limiting movement of the glenoid bearing component relative to the base component along the axis, and placing a second bearing surface of the glenoid bearing component into articulating contact with a third bearing surface of the base component by the movement of the glenoid bearing component along the axis.

DESCRIPTION OF THE PREFERRED EMBODIMENTS

While the shoulder prosthesis assembly described herein is susceptible to various modifications and alternative forms, specific embodiments thereof have been shown by way of example in the drawings and will herein be described in detail. It should be understood, however, that there is no intent to limit the shoulder prosthesis assembly to the particular forms disclosed, but on the contrary, the intention is to cover all modifications, equivalents, and alternatives falling within the spirit and scope of the invention as defined by the appended claims.

Figure 2:
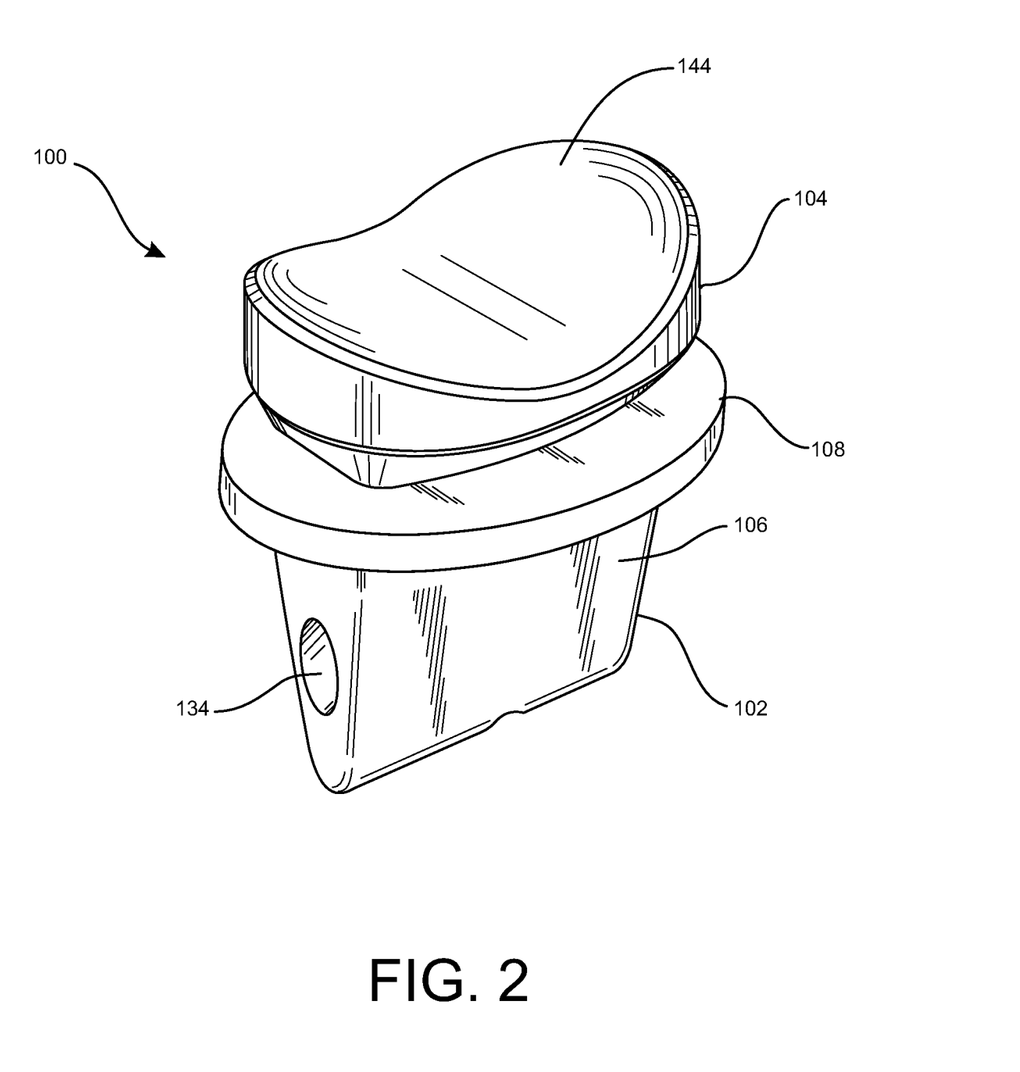
FIG. 2 depicts a perspective view of a shoulder prosthesis assembly of the present disclosure.

Referring now to FIG. 2, there is shown a shoulder prosthesis assembly 100 that is configured to be implanted in a human scapula. The prosthesis assembly 100 includes a glenoid base component 102 and a glenoid bearing 104. The glenoid base component 102 in this embodiment is made entirely of a metallic material, while the glenoid bearing 104 is made entirely of a polymeric material. Preferably, the glenoid base component 102 is made of a biological grade stainless steel or titanium material. Also, the glenoid bearing support may include a porous-coating on its entire outer surface to facilitate biological ingrowth of a patient's bone. The glenoid bearing 104 is preferably made entirely of a polymer such as polyethylene. One particular polyethylene that is well suited for use as the bearing component is a high molecular weight polyethylene, for example, ultra-high molecular weight polyethylene (UHMWPE).

Figure 3:
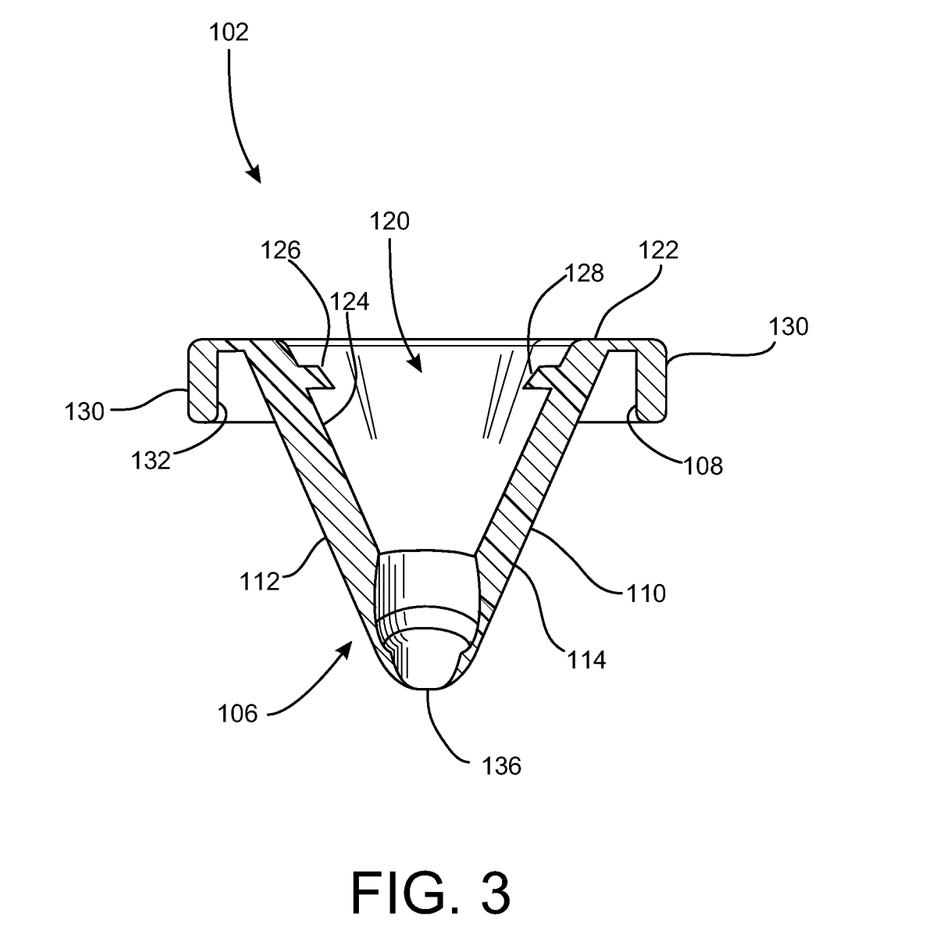
FIG. 3 depicts an end cross-sectional view of the glenoid bearing base of FIG. 2.
Figure 4:
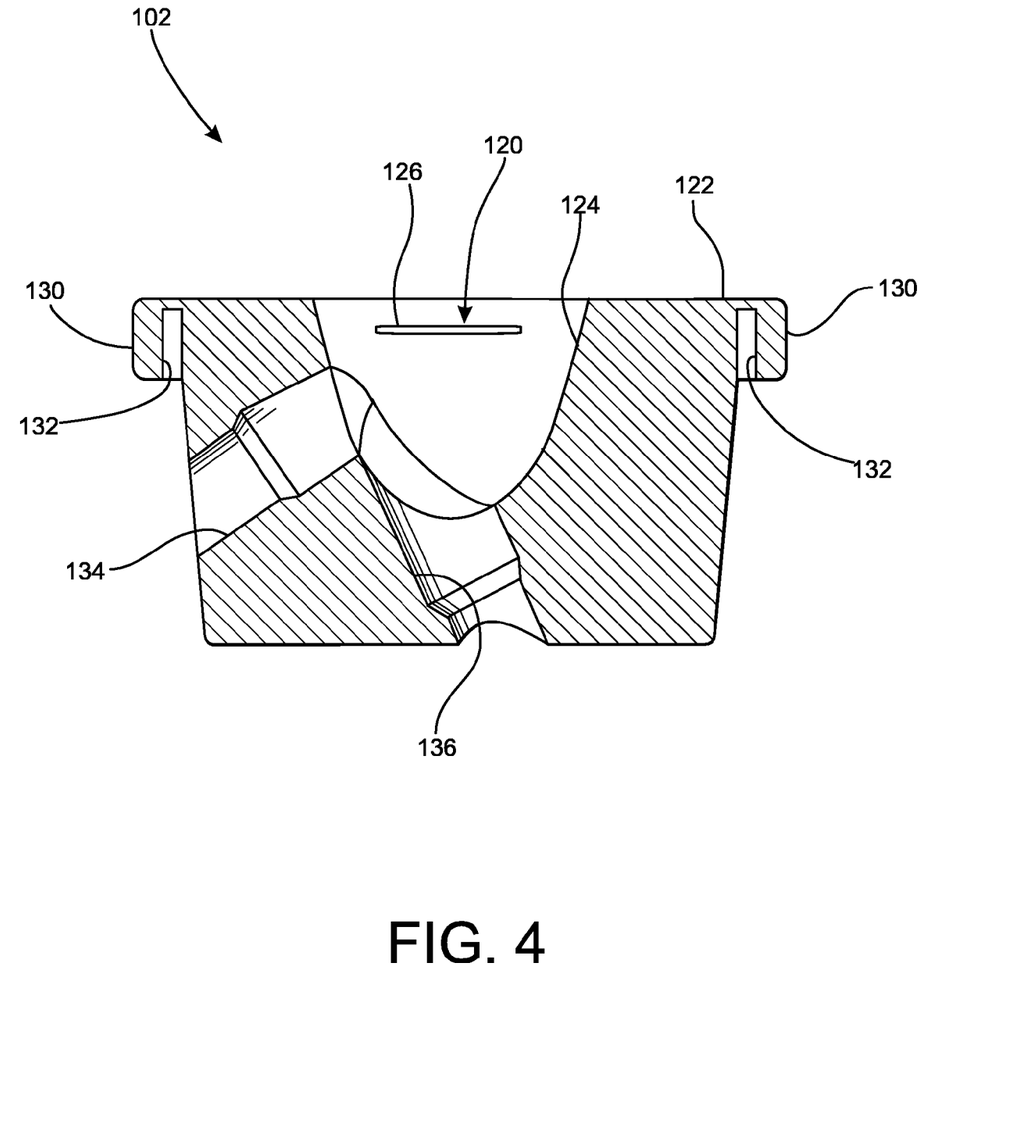
FIG. 4 depicts a side cross-sectional view of the glenoid bearing base of FIG. 2.
Figure 5:
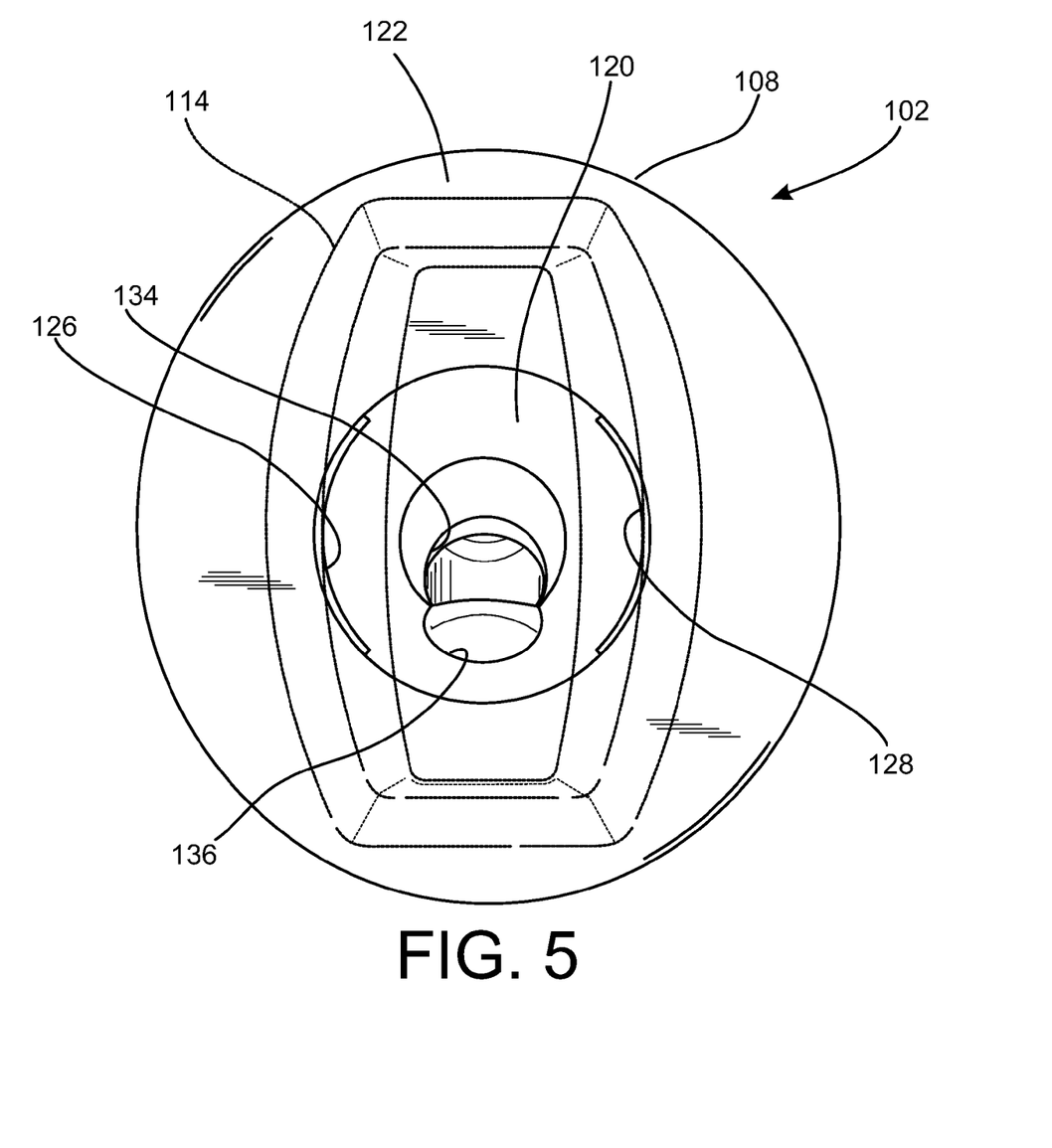
FIG. 5 depicts a top plan view of the base of FIG. 2.

The glenoid base component 102 is described with further reference to FIGS. 3 and 4. In particular, the glenoid base component 102 includes a glenoid vault-occupying portion 106 and a glenoid rim replacement portion 108. The glenoid rim replacement portion 108 is attached to the glenoid vault-occupying portion 106 as shown in FIGS. 3-4. If desired, the glenoid rim replacement portion 108 and the glenoid vault-occupying portion 106 may be attached to each other by being integrally formed together as a single part.

Alternatively, the glenoid rim replacement portion 108 and the glenoid vault-occupying portion 106 may be separately formed. In such embodiments, a cavity may be formed in the glenoid vault-occupying portion 106 which receives a complementary shaped cavity occupying portion of the glenoid rim replacement portion 108. If desired, the separately formed glenoid rim replacement portion 108 and glenoid vault-occupying portion 106 may be attached to each other by snap-fit or friction-fit features or the like. One such friction fit feature is a ball taper connection which allows for version correction of the glenoid rim replacement portion 108 independent of the version of the glenoid vault-occupying portion 106. Alternatively, soft tissue may be relied upon to maintain the glenoid rim replacement portion 108 mated with the glenoid vault-occupying portion 106.

The glenoid vault-occupying portion 106 is configured to occupy at least a portion of the glenoid vault of a scapula, such as the glenoid vault 20 shown in FIG. 1. If desired, the glenoid vault-occupying portion 106 may configured to substantially completely fill the glenoid vault of a scapula, such as glenoid vault 20 shown in FIG. 1. The glenoid vault-occupying portion 106 has an exterior wall 110 and an exterior wall 112 as best shown in FIG. 3. When the glenoid vault-occupying portion 106 is viewed in cross-section (see FIG. 3) the exterior wall 110 and the exterior wall 112 are positioned with respect to each other to define a generally V-shaped wedge 114.

The glenoid vault-occupying portion 106 has a mating portion 120 which extends inwardly from a bearing surface 122. The bearing surface 122 provides support for the glenoid rim replacement portion 108 and may be polished to reduce generation of wear products. The mating portion 120 includes a wall portion 124 which defines a generally cone shaped inner periphery of the base 102. A ridge 126 and a ridge 128 extend into the recess formed by the wall portion 124. The ridges 126 and 128 extend partially along the inner periphery defined by the wall portion 124.

A rim 130 extends from the bearing surface 122. The rim 130 and wedge 114 define a pocket 132 which extends completely about the wedge 114. If desired, bone graft material may be placed into the pocket 132.

The glenoid vault-occupying portion 106 further includes fastener channels 134 and 136. Fasteners may be inserted through the mating recess 120 and through the channels 134 and 136 to affix the glenoid base component 102 to a glenoid.

Figure 6:
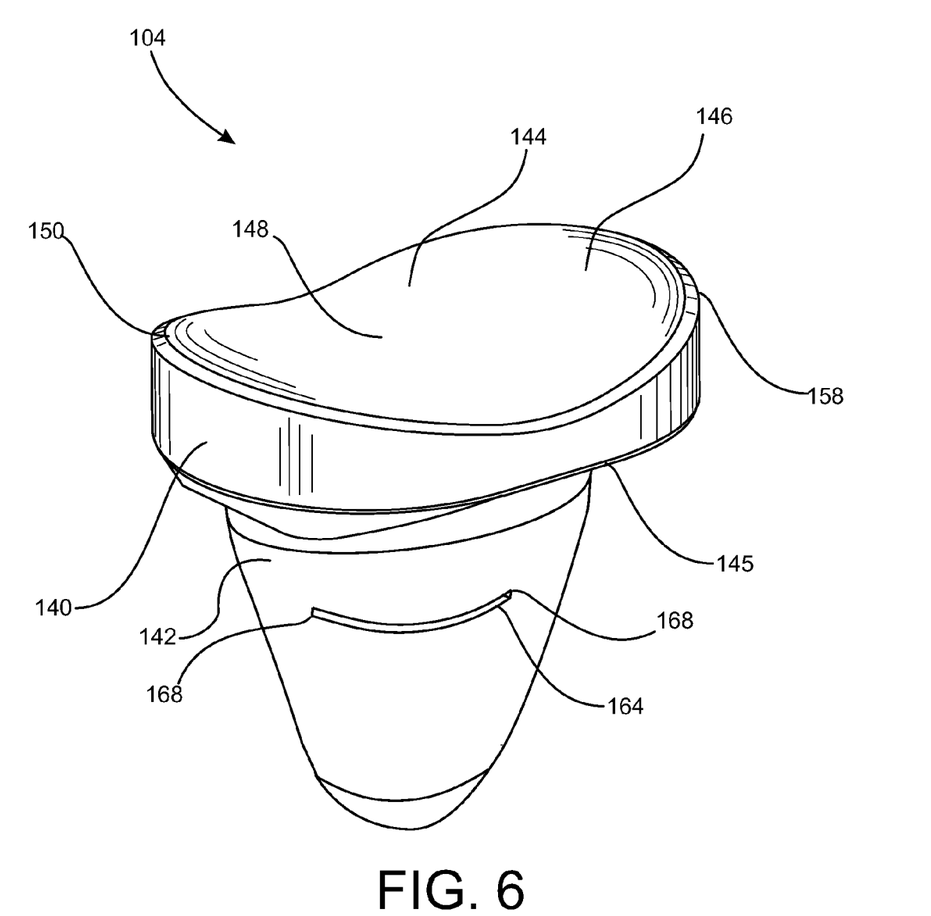
FIG. 6 depicts a perspective view of the glenoid bearing of FIG. 2.
Figure 6A:
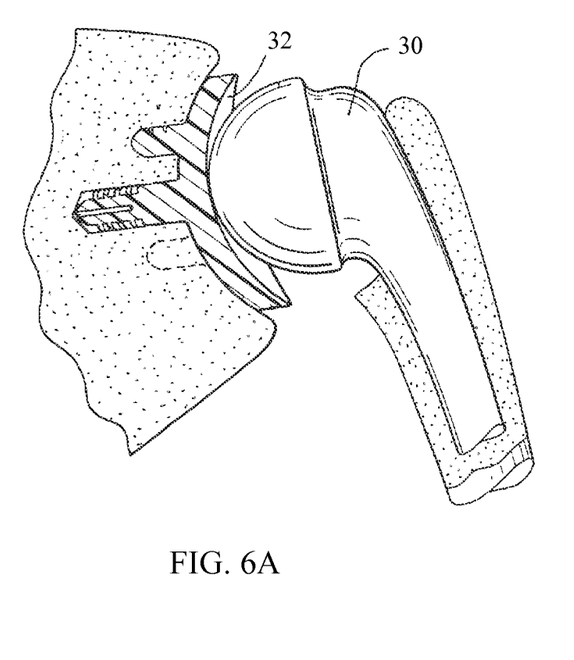
FIG. 6A depicts a cross sectional view of a spherical humeral component that may be used with the glenoid bearing of FIG. 6.
Figure 7:
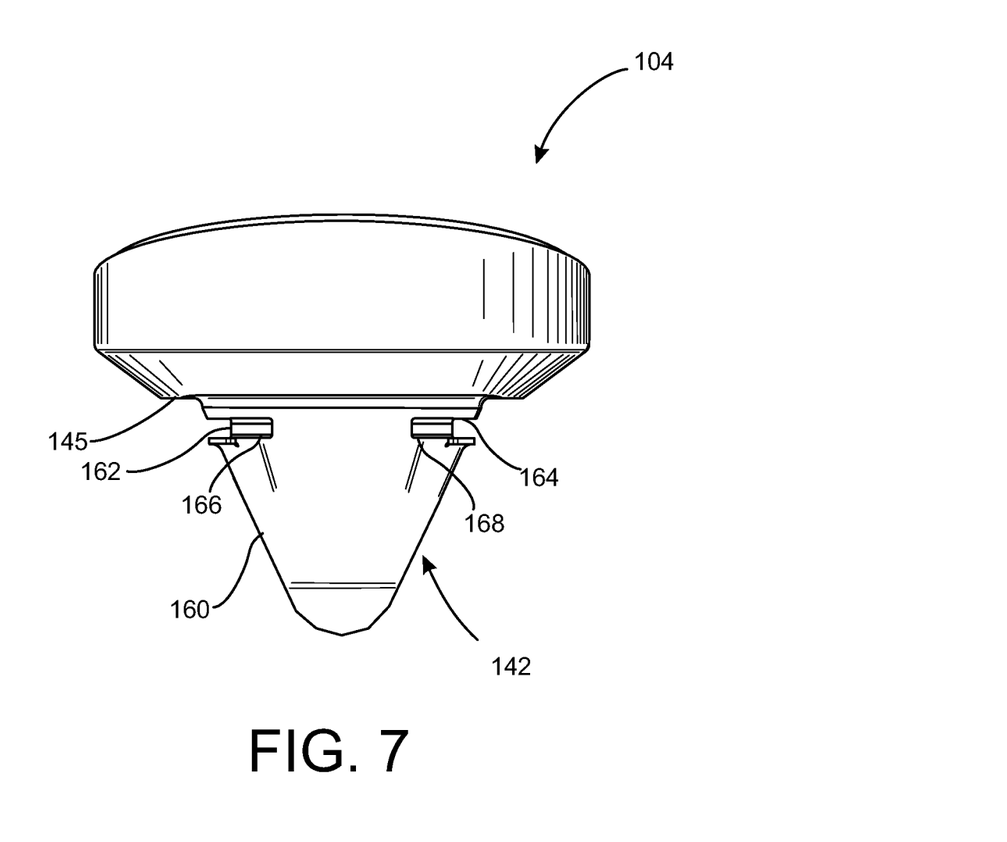
FIG. 7 depicts an end plan view of the glenoid bearing of FIG. 6.
Figure 8:
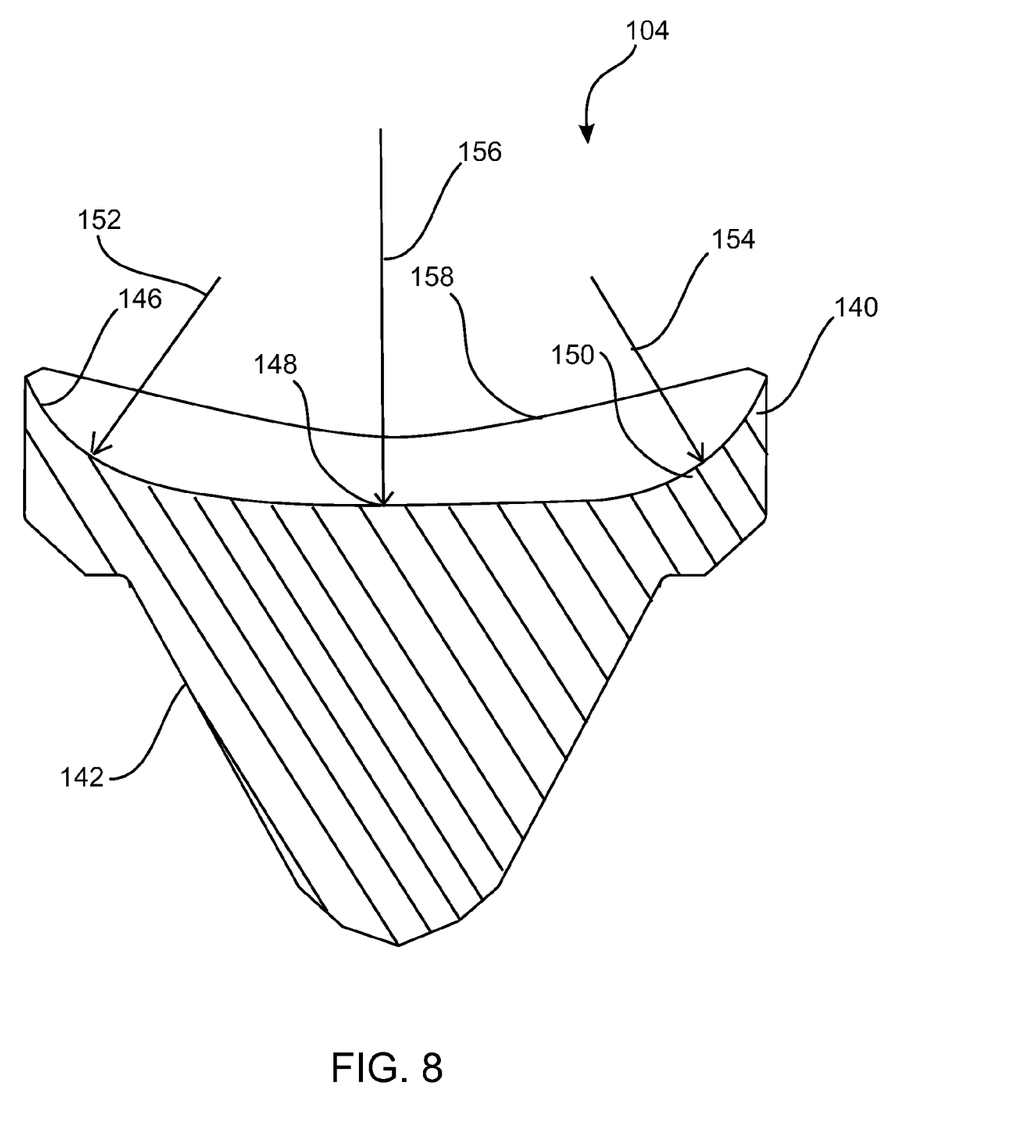
FIG. 8 depicts a side cross-sectional view of the glenoid bearing of FIG. 6.

The glenoid bearing 104 is shown in more detail in FIGS. 6-8. In particular, the bearing 104 includes a body 140 and a mating member 142. The body 140 includes a bearing surface 144 configured to articulate with a spherical humerus component, such as the spherical humeral component 30 shown in FIG. 6A with a glenoid component 32, and a bearing surface 145 configured to articulate with the bearing surface 122.

The glenoid bearing 104 is a stretched bearing. A "stretched bearing" is a bearing that includes a bearing surface with at least three distinct geometries. With reference to FIG. 8, the bearing surface 144 includes an outer bearing portion 146, a central bearing portion 148, and an outer bearing portion 150. The outer bearing portion 146 is spherically shaped with a radius of curvature 152 and the outer bearing portion 150 is spherically shaped with a radius of curvature 154. The radius of curvature 152 is preferably the same length as the radius of curvature 154. The central portion 148, however, has a radius of curvature 156 that is much larger than the radius of curvature 152 and the radius of curvature 154. In some embodiments, the central portion 148 includes a substantially planar portion. A rim 158 extends completely around the bearing surface 144.

The mating member 142 includes a wall 160 that defines a conical outer periphery and slots 162 and 164. The slots 162 and 164 extend inwardly from the outer periphery defined by the wall 160 and are configured to receive the ridges 126 and 128, respectively. The slot 162 includes two end portions 166 and the slot 164 includes two end portions 168. The length of the slots 162 and 164 about the outer periphery defined by the wall 160 is greater than the length of the ridges 126 and 128 about the inner periphery defined by the wall portion 124. The conical shape defined by the wall 160 is complementary to the conical shape defined by the wall portion 124.

The shoulder prosthesis assembly 100 is assembled by implanting the glenoid base component 102 in the glenoid vault 20 of a patient. If desired, fasteners may be inserted through the mating recess 120 and the channels 134 and 136 to affix the base component 102 to the glenoid vault. A glenoid bearing 104 is then selected. The glenoid bearing 104 is selected such that the outer bearing portions 146 and 150 have radii of curvatures 152 and 154 which provide the desired coverage for the diameter of the spherical humeral head that is used. Accordingly, a number of different glenoid bearings 104 may be provided in a kit with a number of different radii of curvature 152 and 154.

The selected glenoid bearing 104 is then coupled with the implanted base component 102 by axially aligning the slots 162 and 164 with the ridges 126 and 128 and inserting the mating member 142 into the mating recess 120. As the mating member 142 is inserted, the mating member 142 contacts the ridges 126 and 128 and the mating member 142 is slightly compressed until the slots 162 and 164 are vertically aligned with the ridges 126 and 128 at which point the mating member 142 decompresses thereby locking the bearing 104 within the mating recess 120. In devices with different radii of curvature 152 and 154, the vertical height of the ridges 126 and 128 may be offset, with a similar offset in the vertical height of the slots 162 and 164 to ensure a desired orientation of the bearing 104 on the base component 102.

Once the bearing 104 is locked with the base 102, the bearing surface 145 is rotatably supported on the bearing surface 122. Rotation of the bearing 104 on the base 102 is provided since the length of the slots 162 and 164 about the outer periphery defined by the wall 160 is greater than the length of the ridges 126 and 128 about the inner periphery defined by the wall portion 124. Rotation is limited by contact of the end portions 166 with the ridge 126 and contact of the end portions 168 with the ridge 128. The extent of rotation may be adjusted by providing slots of differing lengths. By joining the slots, 360 degree rotation may be allowed.

Rotation is effected when the shoulder prosthesis assembly 100 is implanted as the spherical humeral head contacts the ridge 158. At the central portion 148, the curvature of the rim does not complement the curvature of the spherical head. Accordingly, a torque is generated on the bearing 104. The torque causes the bearing 104 to rotate. As the bearing 104 rotates, the spherical head continues to contact the rim 158 until the spherical head moves into one of the outer bearing portions 146 or 150. The radius of curvature of the rim 158 in the outer bearing portions 146 and 150 matches the radii of curvature 152 and 154 in the outer portions 146 and 150. Thus, since the radii of curvature 152 and 154 complement the radius of curvature of the spherical head, the spherical head is captured at the outer portions 146 or 150.

In the embodiment of FIG. 2, rotation of the bearing 104 on the base 102 is limited to less than 360 degrees. Accordingly, the bearing surface 122 need not be circular. Rather, an hour-glass shaped bearing surface may be used to provide rotational support throughout rotation of the bearing 104. Use of a circular bearing surface 122, however, allows a surgeon to use either limited rotation bearings 104 or bearings 104 that can rotate 360 degrees with a single base 102, reducing the number of bases needed in inventory.

Another benefit of a circular bearing surface on a base component can be realized with bases using a conical stem in place of the wedge 114. Specifically, site preparation is simplified for base components incorporating stems and circular bearing surfaces. A guide wire may be used to guide a rotating bone cutting device with multiple cutting edges such that the glenoid vault is shaped to receive the stem and circular bearing surface in a single operation. If desired, fins may be provided on the stem in such base components to prevent rotation of the base component.

In embodiments of the shoulder prosthesis assembly 100 allowing 360 degree rotation, the ridges 126 and 128 and the slots 162 and 164 may be omitted. The vertical height of the mating member 142 and the pressure provided by soft tissue around the shoulder joint are sufficient to maintain the mating member 142 within the mating recess 120. In embodiments incorporating the ridges 126 and 128 and the slots 162 and 164, the vertical height of the mating member 142 may be reduced to provide a truncated cone since the slot/ridge locking mechanism and the pressure provided by soft tissue around the shoulder joint are sufficient to maintain the mating member 142 within the mating recess 120.

While the embodiment of FIGS. 2-8 incorporates a rim replacement vault, various modifications may be made within the scope of the invention. By way of example, FIGS. 9-12 depict a shoulder prosthesis assembly 200 that is configured to be implanted in a vault of a human scapula. The prosthesis assembly 200 includes a glenoid base component 202 and a glenoid bearing 204. The glenoid base component 202 in this embodiment is made entirely of a metallic material, while the glenoid bearing 204 is made entirely of a polymeric material. Preferably, the glenoid base component 202 is made of a biological grade stainless steel or titanium material. Also, the glenoid bearing support may include a porous-coating on its entire outer surface to facilitate biological ingrowth of a patient's bone. The glenoid bearing 204 is preferably made entirely of a polymer such as polyethylene. One particular polyethylene that is well suited for use as the bearing component is a high molecular weight polyethylene, for example, ultra-high molecular weight polyethylene (UHMWPE).

Figures 9, 10, 11, 12:
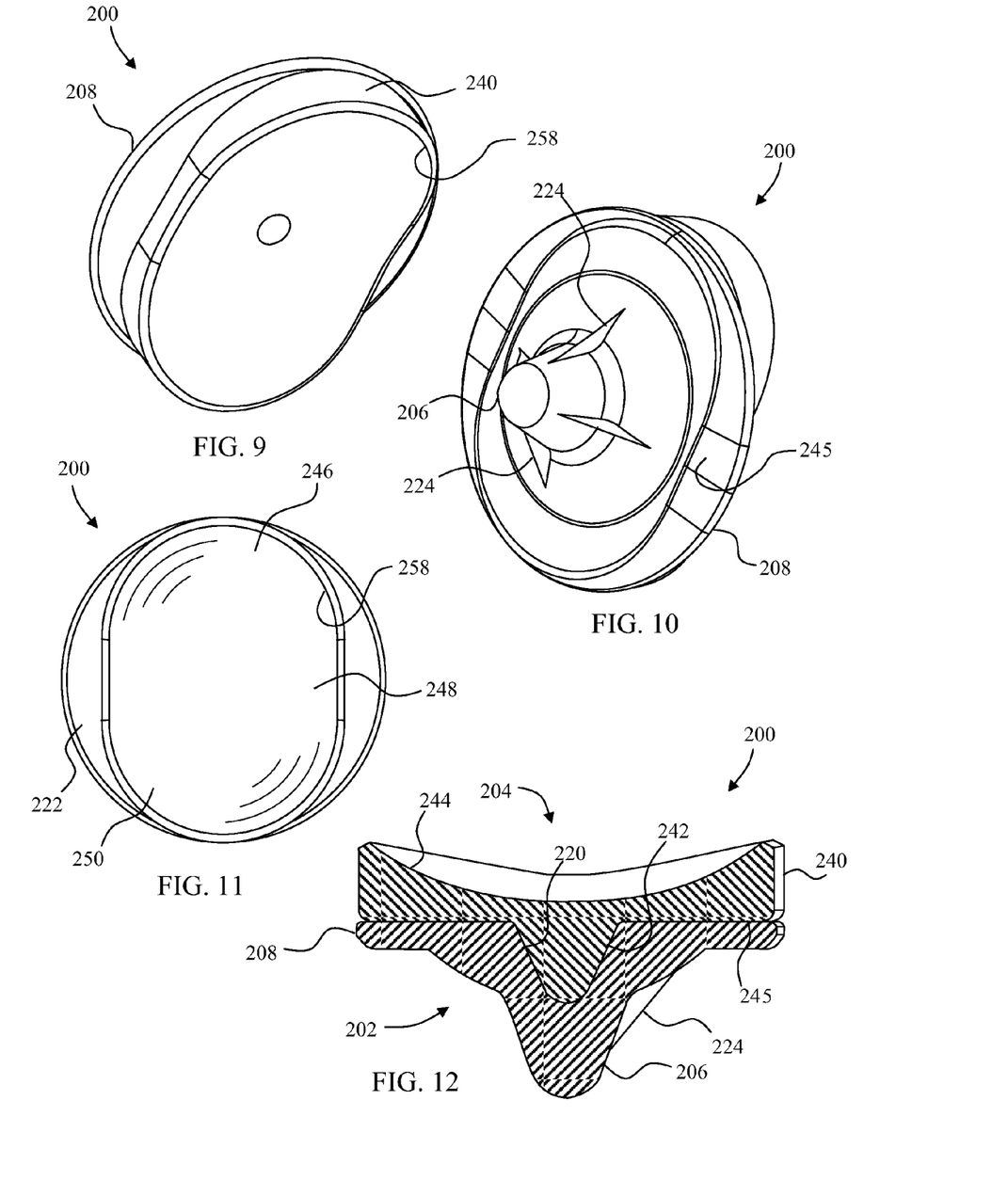
FIG. 9 depicts a top perspective view of a shoulder assembly prosthesis with a stretched bearing component that does not include a rim replacement vault.
FIG. 10 depicts a bottom perspective view of the shoulder assembly prosthesis of FIG. 9.
FIG. 11 depicts a top plan view of the shoulder assembly prosthesis of FIG. 9.
FIG. 12 depicts a cross-sectional view of the shoulder assembly prosthesis.

The glenoid base component 202 includes a stem 206 and a base plate portion 208. If desired, the stem 206 and the base plate portion 208 may be attached to each other rather than being integrally formed together as a single part. The stem 206 is configured to occupy at least a portion of the glenoid vault of a scapula, such as the glenoid vault 20 shown in FIG. 1.

The base component 202 has a mating recess 220 which extends inwardly from a bearing surface 222. The bearing surface 222 provides support for the bearing 204 and may be polished to reduce generation of wear products. The base component 202 further includes a number of fins 224 which prevent rotation of the base component 202 once the base component 202 is implanted.

The glenoid bearing 204 includes a body 240 and a mating member 242. The mating member 242 is shaped complementary to the conical shape of the coupling member 220. The body 240 includes a bearing surface 244 configured to articulate with a spherical humerus component (not shown) and a bearing surface 245 configured to articulate with the bearing surface 222.

The glenoid bearing 204 is a stretched bearing which includes an outer bearing portion 246, a central bearing portion 248, and an outer bearing portion 250. The outer bearing portions 246 and 250 are spherically shaped, preferably with a similar radius of curvature. The central portion 248, however, has a radius of curvature that is much larger than the radius of curvature of the bearing portions 246 and 250. In some embodiments, the central portion 248 includes a substantially planar portion. A ridge 258 extends completely about the periphery of the central bearing portion 248.

The shoulder prosthesis assembly 200 is assembled and operated in substantially the same manner as the shoulder prosthesis assembly 200. One difference is that the glenoid bearing 204 is not rotatably locked to the base component 202. Rather, the pressure provided by soft tissue around the shoulder joint is sufficient to maintain the mating member 242 within the mating recess 220.

Figures 13, 14, 15:
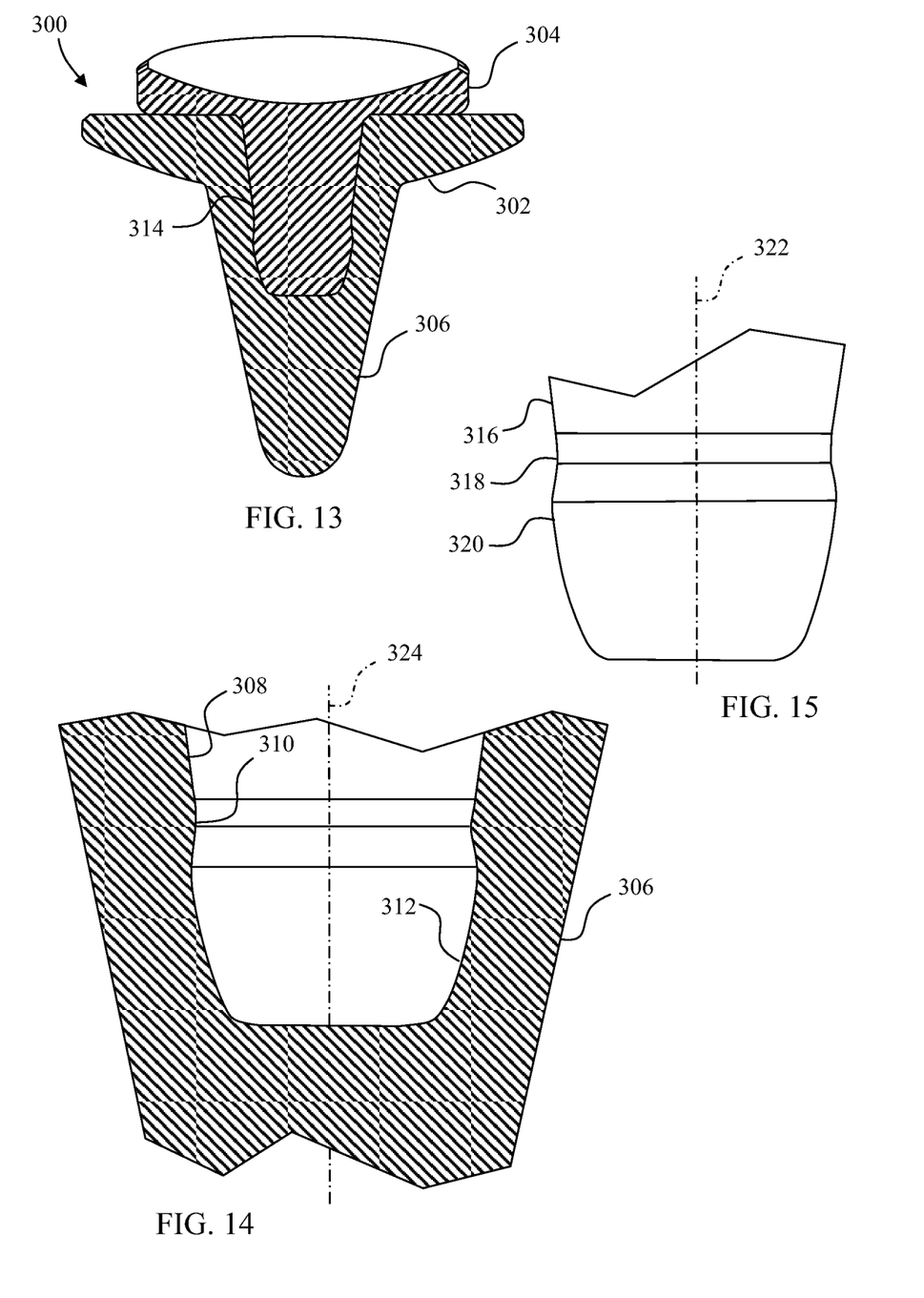
FIG. 13 depicts a cross-sectional view of a shoulder assembly prosthesis with a stretched bearing component which is snap-fit to a base component.
FIG. 14 depicts a partial cross-sectional view of the mating recess of the base component of FIG. 13.
FIG. 15 depicts a partial plan view of the mating portion of the stretched bearing component of FIG. 13.

Rather than relying solely upon pressure provided by soft tissue, vault versions may incorporate friction fit or snap-fit features to maintain the bearing component mated with the base component. By way of example, FIGS. 13-15 depict a shoulder prosthesis assembly 300 that includes a glenoid base component 302 and a stretched glenoid bearing 304.

The base component 302 includes a mating recess 306 with a conical portion 308, a neck 310 and a bulbous void 312. The stretched glenoid bearing 304 includes a mating portion 314 with a conical portion 316, a neck 318 and a bulbous portion 320. The conical portion 316, the neck 318 and the bulbous portion 320 are sized complementary to the conical portion 308, the neck 310 and the bulbous void 312, respectively. The bulbous portion 320, however, has a diameter in a plane orthogonal to the longitudinal axis 322 of the mating portion 306 that is smaller than the diameter of the neck 310 in the plane in which the narrowest portion of the neck 310 lies. Accordingly, the bulbous portion 320 must be compressed somewhat in order to slide the bulbous portion 320 past the neck 310 along the longitudinal axis 324 of the mating portion 306 and into the bulbous void 312. In some embodiments, a void may be formed within the bulbous portion 320 to facilitate compression of the bulbous portion 320.

There is a plurality of advantages arising from the various features of each of the embodiments of the shoulder prosthesis assembly described herein. It will be noted that alternative embodiments of the shoulder prosthesis assembly may not include all of the features described yet still benefit from at least some of the advantages of such features. Those of ordinary skill in the art may readily devise their own implementations of the shoulder prosthesis assembly that incorporates one or more of the features and fall within the spirit and scope of the present invention as defined by the appended claims.

What is claimed is:

1. A method of installing a prosthesis assembly, comprising:
    installing a base component in a prepared glenoid vault;
    selecting a glenoid bearing component including a bearing surface comprising a first articulating portion partially surrounded by a first rim portion, a second articulating portion partially surrounded by a second rim portion, and a third articulating portion partially surrounded by a pair of spaced apart third rim portions, wherein the first rim portion, the second rim portion, and the pair of spaced apart third rim portions define a non-circular shape when projected onto a plane, and the first rim portion has a first radii of curvature on the plane, the second rim portion has a second radii of curvature on the plane;
    axially aligning a plurality of slots in one of the glenoid bearing component and the base component with a plurality of ridges in the other of the glenoid bearing component and the base component, each of the plurality of slots having a maximum length which is greater than a maximum length of a respective one of the plurality of ridges;
    engaging each of the plurality of ridges with the respective one of the plurality of grooves thereby rotatably coupling the glenoid bearing component and the base component and limiting axial movement of the glenoid bearing component relative to the base component; and
    placing the bearing surface into articulating contact with a humeral head.

2. The method of claim 1, further comprising:
    implanting a humeral component, the humeral component including the humeral head.

3. The method of claim 2, wherein placing the bearing surface into articulating contact with the humeral head comprises:
    placing the bearing surface into articulating contact with a spherical humeral head.

4. The method of claim 3, wherein:
the first articulating portion has a third radii of curvature;
the second articulating portion has a fourth radii of curvature;
the spherical humeral head has a fifth radii of curvature;
the pair of spaced apart third rim portions have a sixth radii of curvature;
the third and fourth radii of curvature are complementary to the fifth radii of curvature; and
the sixth radii of curvature is not complementary to the fifth radii of curvature.

5. The method of claim 3, wherein the third articulating portion is substantially planar.

6. The method of claim 1, wherein engaging each of the plurality of ridges with the respective one of the plurality of grooves comprises:
inserting a mating member of the glenoid bearing component into a mating recess of the base component.

7. The method of claim 6, further comprising:
attaching the base component to the prepared glenoid vault by inserting a fastener through a side wall of the mating recess and into the prepared glenoid vault.

8. The method of claim 7, further comprising:
filling with bone graft material a pocket defined between a rim portion of the base component and a wedge portion of the base component, wherein the mating recess is defined within the wedge portion.

9. The method of claim 8, wherein each of the plurality of ridges is coplanar.

10. A method of installing a prosthesis assembly, comprising:
installing a base component in a prepared glenoid vault;
selecting a glenoid bearing component including a first bearing surface comprising a first articulating portion partially surrounded by a first rim portion, a second articulating portion partially surrounded by a second rim portion, and a third articulating portion partially surrounded by a pair of spaced apart third rim portions, wherein the first rim portion, the second rim portion, and the pair of spaced apart third rim portions define a non-circular shape when projected onto a plane;
axially aligning a first locking component of the glenoid bearing component and a second locking component of the base component along an axis perpendicular to the plane;
engaging the first locking component with the second locking component by moving the glenoid bearing component along the axis thereby rotatably coupling the glenoid bearing component and the base component and limiting movement of the glenoid bearing component relative to the base component along the axis; and
placing a second bearing surface of the glenoid bearing component into articulating contact with a third bearing surface of the base component by the movement of the glenoid bearing component along the axis.

11. The method of claim 10, further comprising:
placing the first bearing surface into articulating contact with a humeral head.

12. The method of claim 11, wherein engaging the first locking component with the second locking component comprises;
inserting a substantially conical first portion of the glenoid bearing component into a second mating portion of the base component.

13. The method of claim 12, wherein the first articulating portion and the second articulating portion are spherical and the first bearing surface is non-circular when projected onto the plane.

14. The method of claim 13, wherein installing the base component comprises:
inserting a stem portion within the prepared glenoid vault.

15. The method of claim 14 wherein installing the base component comprises:
inserting at least one fin into the prepared glenoid vault.

16. The method of claim 10, wherein engaging the first locking component with the second locking component comprises:
positioning a first ridge extending from the base component within a first slot formed in the glenoid bearing component.

17. The method of claim 16, wherein engaging the first locking component with the second locking component further comprises:
positioning a second ridge extending from the base component within a second slot formed in the glenoid bearing component, wherein the first and second ridge are coplanar and the first and second slot are not contiguous with each other.

* * * * *